US010099004B2

(12) United States Patent
De Polo

(10) Patent No.: US 10,099,004 B2
(45) Date of Patent: Oct. 16, 2018

(54) EXTRA-CORPOREALLY PORTABLE INFUSION DEVICE

(71) Applicant: Roche Diabetes Care, Inc., Indianapolis, IN (US)

(72) Inventor: Marco De Polo, San Mateo, CA (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 445 days.

(21) Appl. No.: 14/832,536

(22) Filed: Aug. 21, 2015

(65) Prior Publication Data

US 2015/0352277 A1 Dec. 10, 2015

Related U.S. Application Data

(63) Continuation of application No. 12/492,865, filed on Jun. 26, 2009, which is a continuation of application No. PCT/EP2007/064645, filed on Dec. 28, 2007.

(30) Foreign Application Priority Data

Dec. 29, 2006 (CH) ...................................... 2126/06

(51) Int. Cl.
*A61M 5/142* (2006.01)
*A61M 39/02* (2006.01)
*A61M 5/14* (2006.01)

(52) U.S. Cl.
CPC ...... *A61M 5/1413* (2013.01); *A61M 5/14248* (2013.01); *A61M 39/02* (2013.01);
(Continued)

(58) Field of Classification Search
CPC ............ A61M 5/1413; A61M 5/14244; A61M 5/14248; A61M 2005/14252; A61M 2005/14268
See application file for complete search history.

(56) References Cited

U.S. PATENT DOCUMENTS 5,472,317 A 12/1995 Field et al.
5,545,143 A 8/1996 Fischell
(Continued)

FOREIGN PATENT DOCUMENTS

DE 10255817 A1 6/2004
EP 1527792 A1 5/2005
(Continued)

*Primary Examiner* — Quynh-Nhu H Vu
(74) *Attorney, Agent, or Firm* — Dinsmore & Shohl, LLP

(57) ABSTRACT

A portable medical apparatus for administering a fluid drug in doses, including a first housing including a reservoir unit with an outlet into a fluid path for conducting the drug, a second housing including a conveying unit for dispensing the drug from the reservoir unit in doses and a suitable controller for controlling the conveying unit, an adaptor including a coupling structure for receiving the first housing and the second housing and an attaching structure for extra-corporeally carrying the adaptor on a patient, wherein the conveying unit and the reservoir unit can be joined together to form an integrated mechanical and fluidic unit, and coupled to and decoupled from at least two differently configured adaptors, wherein at least one of the adaptors is configured to be directly attached to the surface of the skin and at least one of the adaptors is configured to be worn on or carried by an article of clothing or a wearing system (e.g., a belt).

15 Claims, 2 Drawing Sheets

(52) U.S. Cl.
CPC .......... *A61M 2005/14264* (2013.01); *A61M 2005/14268* (2013.01)

(56) References Cited

U.S. PATENT DOCUMENTS

| | | | | |
|---|---|---|---|---|
| 2003/0088238 A1* | 5/2003 | Poulsen | ............ | A61M 5/1413 604/890.1 |
| 2003/0153900 A1 | 8/2003 | Aceti et al. | | |
| 2004/0059316 A1 | 3/2004 | Smedegaard | | |
| 2005/0171512 A1 | 8/2005 | Flaherty | | |
| 2006/0015063 A1 | 1/2006 | Buetikofer et al. | | |
| 2006/0264890 A1 | 11/2006 | Moberg et al. | | |
| 2008/0077081 A1* | 3/2008 | Mounce | ............ | A61M 5/1413 604/67 |
| 2008/0097326 A1* | 4/2008 | Moberg | ............ | A61M 5/1413 604/155 |
| 2008/0214916 A1* | 9/2008 | Yodfat | ............... | A61B 5/14532 600/347 |
| 2008/0319414 A1* | 12/2008 | Yodfat | ................ | A61B 5/6849 604/506 |
| 2010/0137790 A1* | 6/2010 | Yodfat | ............ | A61M 5/14248 604/67 |

FOREIGN PATENT DOCUMENTS

| | | |
|---|---|---|
| EP | 1682203 B1 | 1/2010 |
| WO | 2004110526 A1 | 12/2004 |
| WO | 2006120253 A2 | 11/2006 |

* cited by examiner

EXTRA-CORPOREALLY PORTABLE INFUSION DEVICE

CROSS-REFERENCE TO RELATED APPLICATIONS

This application is a continuation of U.S. application Ser. No. 12/492,865 filed Jun. 26, 2009, which is a continuation of International Patent Application No. PCT/EP2007/064645, filed on Dec. 28, 2007, which claims priority to Swiss Patent Application No. 02126/06, filed on Dec. 29, 2006, the entire contents of both of which are incorporated herein by reference.

BACKGROUND

The present invention relates to devices for delivering, injecting, infusing, administering or dispensing a substance, and to methods of making and using such devices. More particularly, it relates to a portable medical device or apparatus for dispensing a fluid drug and, in some embodiments, for automatically dispensing the fluid drug.

Devices for automatically and continuously dispensing fluid drugs are often used with patients who continuously require a drug which can be exclusively administered subcutaneously, wherein the requirement varies throughout the day. Specific application scenarios include, for example, certain pain therapies and the treatment of diabetes mellitus, in which computer-controlled administering devices which can be worn on the body are used, wherein there is a fundamental need for the administering device to have a low weight and a minimum volume to enable it to be worn comfortably and discreetly.

Conventional, extra-corporeal infusion devices for therapeutic use which are carried on the body or in clothing by a wearing system are common in the prior art. While the patient is sleeping, they are in most cases placed on or in a storage location next to the bed and remain connected to the body via a catheter supply line, thus maintaining the administering of fluid.

Miniaturised infusion devices have recently become available which are attached directly to the surface of the skin. The administering device is attached to the surface of the skin and the administering cannula is inserted into the body tissue by the patient personally. Once such an infusion device has been attached to the surface of the skin, it generally adheres to the body for 4 to 5 days and is then completely or partially disposed of.

Both infusion devices which are attached to the surface of the skin and conventional infusion devices exhibit situation-dependent advantages and disadvantages specific to their type. Thus, for example, it is desirable during daily use by the patient for the infusion device to be temporarily removable, at least partially, to, for example, pursue a sporting activity without hindrance or to not expose precision parts or electronic components of the administering device to undesirable contact with water in the course of showering or bathing.

A conventional administering device can be temporarily removed by temporarily disconnecting the catheter tube and suitably sealing the coupling locations. Single-use auxiliary devices or features, for example insulin ampoules, batteries and/or catheters, can also be replaced or exchanged without any problems in the conventional administering devices, since the devices are designed for a long service life.

By contrast, administering devices which are worn on the surface of the skin typically may not be temporarily disconnected nor can parts of the device be exchanged due to their design which is consistently oriented toward single use and low production costs. Temporarily disconnecting them from the body in a way suitable for the patient, for physical activities such as, for example, sports, swimming or cleaning the body, is not possible. Even if administering devices which are worn on the surface of the skin are significantly miniaturised, the patient remains restricted in their freedom of movement, since a certain component volume is still arranged on the body, and a static imbalance limits the wearing comfort. There is also the danger of the apparatus detaching from the body because it is insufficiently adhered to the body, for example when attached by means of a plaster, or of the apparatus being torn from the body by sudden movements. The injection locations and wearing locations are also limited for this design. Nonetheless, such devices provide an inconspicuous, discreet way of being worn and short fluid connections which may be cited as advantages of administering devices which are worn on the surface of the skin.

EP 1527792 A1 describes an administering device which can be attached on the surface of the skin, but which cannot be temporarily disconnected.

SUMMARY

It is an object of the present invention to provide a portable medical device or apparatus for administering a fluid drug in doses, which optionally can be worn directly on a surface of the body and/or can be carried by the patient in a conventional way, depending on what is desired and/or suitable.

In one embodiment, the present invention comprises an extra-corporeally portable infusion device which comprises: a reservoir unit comprising a reservoir for a fluid drug and a conveying unit for dispensing the drug in doses. The conveying unit comprises a suitable mechanism or mechanisms for conveying the drug and delivering it in doses.

The present invention is not restricted to administering insulin, but rather generally encompasses administering products which can be administered by infusion or injection. Comparable apparatus can be used not only for self-administering but also in an inpatient environment, for example under the constant supervision of a physician in clinics, for example during recovery or other aftercare, in which they are worn by the patient.

In one embodiment, the present invention comprises a portable medical apparatus for administering a fluid drug in doses, including a first housing including a reservoir unit with an outlet into a fluid path located downstream of the reservoir unit for conducting the drug, a second housing including a conveying unit for dispensing the drug from the reservoir unit in doses and a suitable controller for controlling the conveying unit, an adaptor including a coupling structure for receiving the first housing together with the reservoir unit and the second housing together with the conveying unit, and an attaching structure for extra-corporeally carrying the adaptor on the patient, wherein the conveying unit and the reservoir unit can be joined together to form a mechanical and fluidic overall unit, and coupled to and decoupled from at least two differently configured adaptors to form a mechanical and fluidic whole, and wherein at least one of the adaptors is provided for being directly attached to the surface of the skin and at least one of the adaptors can be worn on or carried by an article of clothing or an accessory or wearing system (e.g., a belt, suspenders, etc.).

In one preferred embodiment of an administering device in accordance with the present invention, the device is designed such that the conveying unit and the reservoir unit can be mechanically and functionally joined together and/or separated by a suitable coupling mechanism or structure, wherein the conveying unit, the reservoir unit and an adaptor, which can comprise a flexible or—as applicable—rigid adaptor plate for resting on clothing or directly on the body, are combined to form an integrated unit.

In some preferred embodiments, one or more coupling means is/are formed on the conveying unit and one or more coupling means is/are formed on the reservoir unit, each such that it cannot be removed without a tool, for example by being integrally molded to the respective housing or connected to it in a material fit or otherwise fixedly joined, for example screwed, to it. This provides the advantage that the coupling means are molded or connected to the respectively assigned unit of the two units such that they cannot be lost, and are therefore available at any time.

In one preferred embodiment, the reservoir unit and the conveying units of the administering device (e.g., a pump) are coupled to a fluidic-mechanical connector of the adaptor which both fixes the units relative to the adaptor or the adaptor plate, and ensures a fluidic connection between the reservoir unit and a cannula which infuses the body, for e.g., a subcutaneous administering. The connector may be advantageously arranged in the middle of the adaptor plate. The mechanical coupling to the connector can be a force-fit coupling achieved by clamping onto the connector or a positive-fit coupling achieved by forming a counter contour using the connected housing parts of the reservoir unit and conveying unit.

In another preferred embodiment, a device in accordance with the present invention comprises a coupling means embodied such that the reservoir unit and the conveying unit can be joined together by moving them relative to each other, for example along rigid guides, e.g. by being pushed together along linear guides such as linear dovetail guides, or by a bayonet lock formed by the two units. This type of coupling enables the two units to be positioned precisely with respect to each other and also facilitates personally joining together the reservoir unit and conveying unit at inaccessible or difficult-to-view locations, for example at an adaptor plate which is laterally attached to a persons belt.

In some preferred embodiments, the coupling means is embodied such that the conveying unit and the reservoir unit can be joined together by latch or snap-in, complementary latching elements. Such coupling means generally manage without additional securing means.

In yet another preferred embodiment, the coupling means is embodied such that the reservoir unit and the conveying unit are joined together in a force fit, e.g. by being clamped or temporarily adhered by a magnetic force or via a Velcro coupling. The coupling means can likewise be embodied such that the reservoir unit and the conveying unit are joined together by expanding one or more rubbery or elastic positive elements formed by the unit, which—when the reservoir unit and the conveying unit are joined together—form(s) an elastically biased positive fit with assigned, rigid positive elements of the complementary unit by enclosing or engaging with one or more counter contours. This enables a zero-clearance coupling to be realized in a cost-effective and simple way.

In one preferred embodiment, the units are attached to the surface of the skin by an adaptor comprising one adaptor plate which remains on the surface of the skin while the administering device is temporarily disconnected and forms a so-called retained part, via a releasable adhesive connection or a skin plaster. This embodiment combines the advantages of the ability to discreetly wear the extra-corporeal infusion devices which are attached to the body with the patient-friendly ability to be temporarily disconnected.

In another preferred alternative embodiment, the pump parts are coupled to a wearing system of the patient, via an adaptor comprising one adaptor plate, to be carried. Such an adaptor plate is embodied such that means for connecting it to a wearing system, e.g. a pendant strap, a belt strap encircling the body, a belt clip or a way of being attached to an item of clothing, are available. This enables the infusion device to be simply adapted to different everyday situations and/or uses by exchanging the wearing system. The device, comprising the pump parts and the adaptor plate, can be worn as a whole on a belt. For this purpose, a lateral cannula connector on the adaptor plate is needed. One or more attaching clips or a belt strap can be attached to the plane underside of the adaptor plate thus created.

In another preferred embodiment using an adaptor plate for carrying on a wearing system, a catheter head which can be disconnected—comprising a cannula for inserting into the body tissue—is connected to the adaptor plate via a short catheter line. Catheter heads which can be disconnected are known in the prior art and are routinely used in pump therapy. In such an embodiment, a septum on the fluidic-mechanical connector of the adaptor plate is unnecessary.

In yet another preferred embodiment of a portable medical device in accordance with the present invention, the coupling means comprise securing means by which the reservoir unit and the conveying unit can be secured against being unintentionally separated, when they are properly joined together, wherein the securing means requires a manipulation to release their lock or connection, which is different than the manipulation required for separating them, e.g. pressing a release button if a rotational movement is required for separating. This enables an optimal degree of security against unintentional separation and loss.

In another preferred embodiment, means—e.g. electronic means—are provided on the device which bring about a secured resting state of the infusion device before separation and enable administering to be continued as planned after joining together.

In some embodiments of the present invention, the conveying unit optionally consists of a conveying unit for single use or for repeated use, the reservoir unit optionally consists of a reservoir unit for single use or for repeated use, and the adaptor plates are optionally embodied for single use or for repeated use.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1:
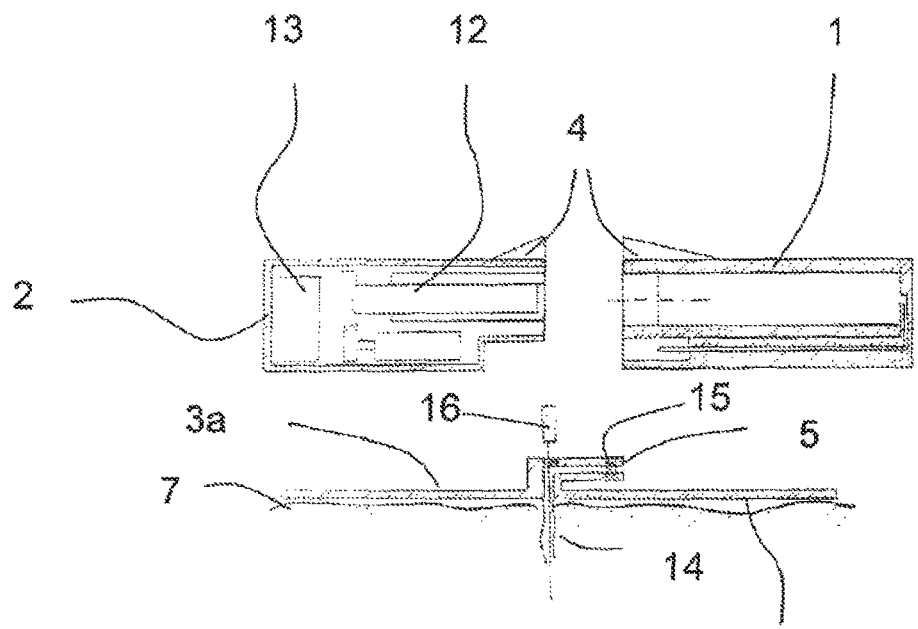
FIG. 1 depicts an embodiment of the present invention comprising a reservoir unit, a conveying unit and an adaptor plate for directly attaching to the surface of the skin.

FIG. 1 shows an infusion device in accordance with the present invention, comprising a conveying unit (2) which can be coupled to a reservoir unit (1) which is attached to the surface of the skin (7) by an adaptor plate (3a). Because the infusion device is completely attached to the surface of the body, large gravitational and acceleration forces may arise in certain circumstances. Accordingly, a suitably strongly adhesive plaster (6) has to be selected which adheres well, but at the same time is simple to remove.

The disadvantages of an apparatus which is permanently attached to the body can be solved by attaching the reservoir unit (1) and the conveying unit (2)—which contains the drive unit (12) and the electronics (13)—to the body via an adaptor. The adaptor comprises an adaptor plate (3a) which rests on the skin, and a fluidic-mechanical connector (5) which projects from it. The units (1) and (2) can be detached from the adaptor plate (3a) via the connector (5) by simple hand movements, while the adaptor plate (3a) can remain on the body, and can thus be temporarily removed from the body to, for example, pursue a sporting activity without hindrance or to not expose precision parts or electronic components of the administering device to undesirable contact with water in the course of showering or bathing. The conveying unit (2), the reservoir unit (1) and the adaptor (3a, 5) are connected by a suitable coupling structure or means (4) which act by being snapped, screwed or by using a quick-release lock (for example levers and belts, a clasp, etc.). The adaptor (3a, 5), comprising an integrated cannula (14) for inserting into the body tissue (7), serves as a connecting and attaching system for the insulin pump and connects the conveying unit (2) to the reservoir unit (1). A septum (15) prevents body fluid from exiting the body while the device is temporarily disconnected. An injection needle (16) which can be inserted on the fluidic-mechanical connector (5) allows the body tissue (7) to be penetrated when the cannula (14) is applied, wherein the reservoir unit can be used as a bearing or carrying housing part, with the advantage that the apparatus unit as a whole can be designed to be very compact and flat. An additional ampoule compartment, such as is used in conventional insulin pumps, is omitted in this arrangement. Handling is likewise simplified, since an additional adaptor is not needed to mechanically connect the reservoir unit (1) and the conveying unit (2) to the cannula (14) and fluidically connect the reservoir unit (1) to the cannula (14), wherein the reservoir unit (1) is designed such that additional conveying as a result of external forces cannot occur due to reinforcements provided (for example, ribs).

Figure 2:
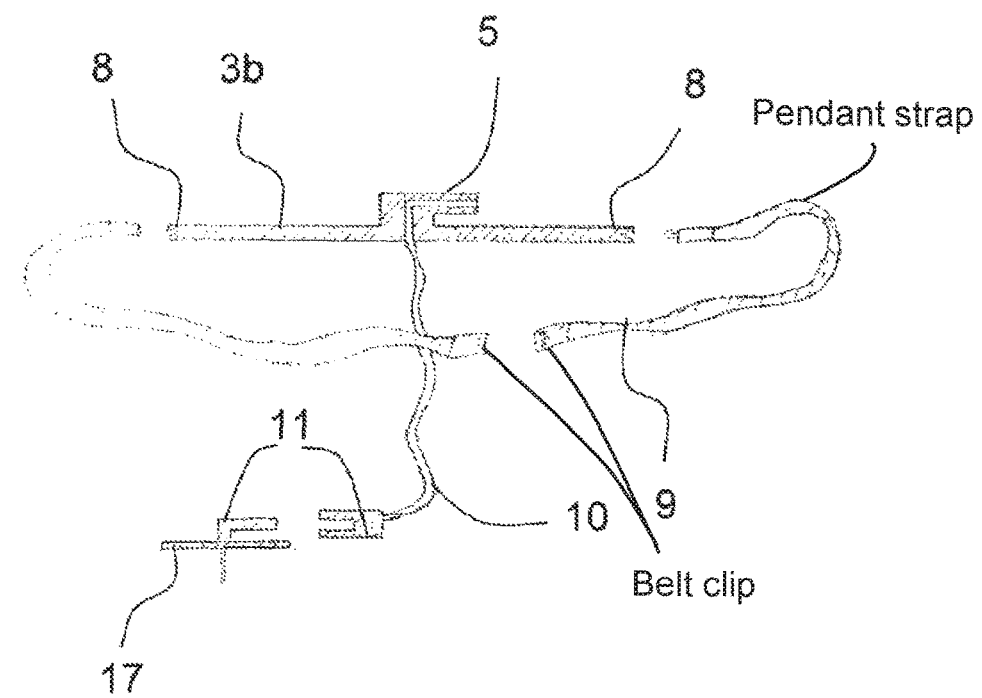
FIG. 2 depicts an adaptor plate for carrying on a wearing system in the form of a belt encircling the body, wherein a short catheter tube piece is attached to the adaptor plate and spans the distance between the wearing position and the cannula injection position.

FIG. 2 shows an embodiment of an adaptor plate (3b) in accordance with the present invention, the plate 3b for an administering device which is carried on the patient's body via a wearing system. As an alternative to being worn attached to the body by the adaptor plate (3a), the reservoir unit (1) and the conveying unit (2) can be combined with the adaptor plate (3b) which enables the fluidic connection to the catheter head (11) via a short (e.g., <50 cm) catheter (10) and can be carried on the body by the patient by, e.g., a belt wearing system (8, 9). Since the forces are largely absorbed via the wearing system, it is possible to use a smaller plaster (17) for attaching the cannula, which reduces the danger of skin irritation and can reduce attaching problems. To enable the infusion device to be temporarily disconnected, the catheter head is embodied such that it can be disconnected. Decoupling the reservoir unit (1) and the conveying unit (2) is not absolutely necessary in this case. The septum in the connector is also unnecessary in this case.

Figure 3:
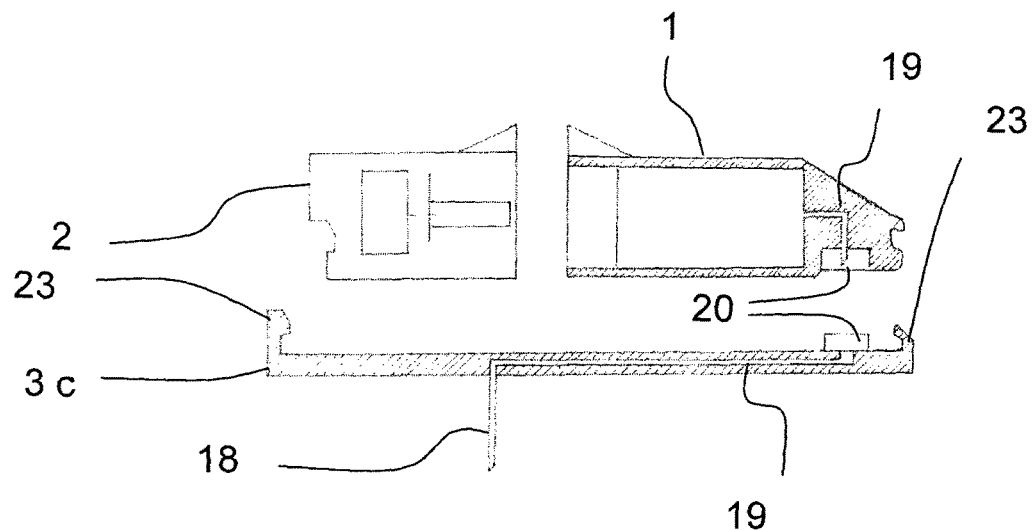
FIG. 3 depicts an adaptor plate for directly attaching to the surface of the skin, wherein the fluid supply line runs in the adaptor plate.

FIG. 3 shows another embodiment of an adaptor plate (3c) for direct attachment to the surface of the skin, in which a catheter supply line (19) is integrated into the adaptor plate downstream of the reservoir unit (1) and can be worn directly on the surface of the skin. The cannula (18) is arranged in the middle of the adaptor plate (3c) and surrounded by a symmetrically arranged skin plaster or adhesive. This arrangement means that the forces which act on the injection location are the same on all sides, thus increasing the wearing comfort. The reservoir unit (1) and the adaptor unit (3c) are fluidically connected using a septum/needle connector (20). The mechanical connection is provided via a mechanical coupling means (23) arranged on the respectively facing side.

Figure 4:
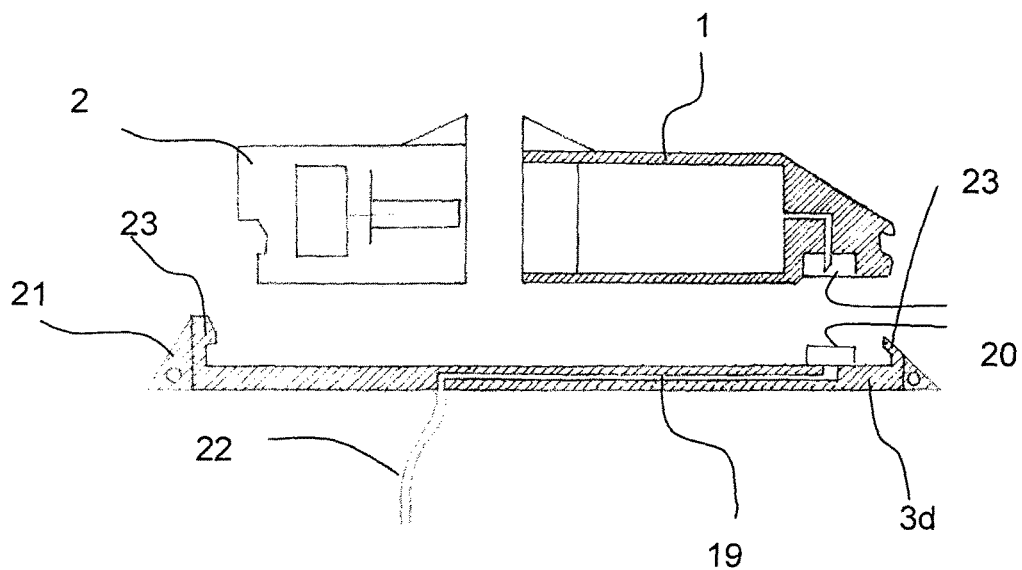
FIG. 4 depicts an adaptor plate for carrying on a wearing system, wherein the fluid supply line runs in the adaptor plate.

FIG. 4 shows an embodiment of an adaptor plate (3d) which is provided for carrying on a wearing system. The reservoir unit and the adaptor unit (3d) are fluidically connected via a septum/needle connector (20); the connecting catheter supply line (19) is integrated into the adaptor plate. The mechanical connection is provided via mechanical coupling structure (23) arranged on the respectively facing side. The catheter supply line (22) which leads downstream is attached, fixedly or releasably, to the adaptor plate. In a representation which is not shown, the catheter supply line can also lead laterally away from the adaptor plate, for example to enable it to be attached to a belt. Suitable attaching structures (21) for attaching the plate 3d to a wearing system are attached to or carried by the facing-side ends of the adaptor plate (3d).

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A portable medical system for administering a fluid drug in doses, comprising:
   a) a first housing comprising a reservoir unit including an outlet into a fluid path located downstream of the reservoir unit for conducting the drug;
   b) a second housing comprising a conveying unit for dispensing the drug from the reservoir unit in doses and a controller for controlling the conveying unit;

c) at least two differently configured adaptors receiving the first housing together with the reservoir unit and the second housing together with the conveying unit wherein d) the conveying unit and the reservoir unit can be joined together without using tools, and reversibly coupled to each of the adaptors without using the tools, and wherein at least one of the adaptors is provided for direct attachment to a skin surface and at least one of the other adaptors can be worn on an item of clothing or carried by a wearing system; and e) wherein the adaptors each has a pair of mechanical connectors which receive and engage releasably in opposition the first housing and the second housing.

2. The portable medical system of claim 1 wherein mechanical and functional coupling of the conveying unit and the reservoir unit is via a coupling means formed by the conveying unit and the reservoir unit.

3. The portable medical system of claim 1 wherein the conveying unit, the reservoir unit and the at least one of the adaptors can be connected to each other via a force-fit or positive-fit connection which can be established without using the tools.

4. The portable medical system of claim 1 wherein the conveying unit and the reservoir unit can be fluidically connected to an outlet of the at least one of the adaptors.

5. The portable medical system of claim 1 wherein the conveying unit and the reservoir unit can be joined together in a positive fit or in a force fit on a fluidic-mechanical connector of the at least one of the adaptors.

6. The portable medical system of claim 1 wherein the conveying unit and the reservoir unit can be joined together in a force fit or in a positive fit.

7. The portable medical system of claim 1 wherein the at least one of the adaptors that is provided for direct attachment to a skin surface comprises a releasable adhesive connection or a skin plaster to couple the portable medical apparatus to the skin surface.

8. The portable medical system claim 1 wherein the at least one of the other adaptors that can be worn on the item of clothing or carried by the wearing system comprises a pendant strap, a belt strap encircling a body, a belt clip or a way of being attached to the item of clothing for connecting to the wearing system.

9. The portable medical system of claim 1 wherein the coupling structure is configured to prevent unintentional separation of the reservoir unit and the conveying unit.

10. The portable medical system of claim 9 wherein the coupling structure is configured such that two different manipulations is required to separate the reservoir unit and the conveying unit.

11. The portable medical system of claim 1 further comprising a catheter head which can be disconnected via a catheter line to the portable medical apparatus to infuse the drug.

12. The portable medical system of claim 1 wherein the conveying unit is for one of a single use or repeated use.

13. The portable medical system of claim 1 wherein the reservoir unit is for a single use.

14. The portable medical system claim 1 wherein the at least one of the adapter which can be attached to the skin surface is for a single use.

15. The portable medical system of claim 1 wherein the wearing system is configured to encircle a body of the patient.

* * * * *